(12) United States Patent
Lasarov et al.

(10) Patent No.: US 11,051,728 B2
(45) Date of Patent: Jul. 6, 2021

(54) APPARATUS COMPRISING A LIGHT DETECTOR, A LIGHT SOURCE AND OPTICS

(71) Applicant: Nokia Technologies Oy, Espoo (FI)

(72) Inventors: Harri Lasarov, Espoo (FI); Antti Salo, Espoo (FI); Teemu Ahmaniemi, Helsinki (FI)

(73) Assignee: NOKIA TECHNOLOGIES OY, Espoo (FI)

( * ) Notice: Subject to any disclaimer, the term of this patent is extended or adjusted under 35 U.S.C. 154(b) by 107 days.

(21) Appl. No.: 15/736,237

(22) PCT Filed: Jun. 2, 2016

(86) PCT No.: PCT/FI2016/050395
§ 371 (c)(1),
(2) Date: Dec. 13, 2017

(87) PCT Pub. No.: WO2017/001722
PCT Pub. Date: Jan. 5, 2017

(65) Prior Publication Data
US 2018/0168495 A1   Jun. 21, 2018

(30) Foreign Application Priority Data

Jun. 30, 2015   (EP) .................................... 15174687

(51) Int. Cl.
*A61B 5/024*   (2006.01)
*A61B 5/1455*   (2006.01)

(52) U.S. Cl.
CPC ...... *A61B 5/14552* (2013.01); *A61B 5/02427* (2013.01); *A61B 2562/0238* (2013.01); *A61B 2562/0242* (2013.01)

(58) Field of Classification Search
USPC ....................................... 600/310, 322, 323
See application file for complete search history.

(56) References Cited

U.S. PATENT DOCUMENTS

| 4,880,304 | A | | 11/1989 | Jaeb et al. | |
|---|---|---|---|---|---|
| 5,995,856 | A | * | 11/1999 | Mannheimer | ...... A61B 5/14552 600/322 |
| 8,131,332 | B2 | * | 3/2012 | Maynard | .............. A61B 5/0071 600/310 |

(Continued)

FOREIGN PATENT DOCUMENTS

CN   104207756   12/2014

OTHER PUBLICATIONS

Patel et al., "A Review of Wearable Sensors and Systems With Application in Rehabilitation", Journal of NeuroEngineering and Rehabilitation, Apr. 20, 2012, pp. 1-17.

(Continued)

*Primary Examiner* — Jason M Sims
*Assistant Examiner* — James Stewart Stambaugh, III
(74) *Attorney, Agent, or Firm* — McCracken & Gillen LLC

(57) ABSTRACT

An apparatus comprising: a light detector; a light source, laterally offset from the light detector by a first lateral offset; optics configured to receive light emitted by the light source and output the received light, wherein a majority of the light output is directed towards an offset region laterally offset from the light detector by at least a second lateral offset different from the first lateral offset.

14 Claims, 2 Drawing Sheets

(56) References Cited

U.S. PATENT DOCUMENTS

| | | | |
|---|---|---|---|
| 8,463,345 B2 | 6/2013 | Kuhn et al. | |
| 2001/0003793 A1* | 6/2001 | Steuer | A61B 5/0261 600/504 |
| 2001/0039376 A1 | 11/2001 | Steuer et al. | |
| 2002/0183623 A1 | 12/2002 | Tang et al. | |
| 2003/0181796 A1 | 9/2003 | Pologe | |
| 2005/0043600 A1* | 2/2005 | Diab | A61B 5/02427 600/344 |
| 2007/0201788 A1 | 8/2007 | Liu et al. | |
| 2008/0021330 A1 | 1/2008 | Hwang et al. | |
| 2008/0265145 A1* | 10/2008 | Uchida | F02B 55/14 250/226 |
| 2009/0182209 A1* | 7/2009 | Benni | A61B 5/14553 600/323 |
| 2011/0066013 A1* | 3/2011 | Harrold | A61B 5/14552 600/323 |
| 2011/0190605 A1* | 8/2011 | Yamashita | A61B 5/02427 600/310 |
| 2011/0237908 A1* | 9/2011 | Sato | A61B 5/02427 600/310 |
| 2012/0130257 A1* | 5/2012 | Heanue | A61B 5/0059 600/476 |
| 2012/0197093 A1 | 8/2012 | LeBoeuf et al. | |
| 2013/0289414 A1* | 10/2013 | Adibnazari | A61B 5/443 600/476 |
| 2014/0107493 A1 | 4/2014 | Yuen et al. | |
| 2014/0206954 A1 | 7/2014 | Yuen et al. | |
| 2014/0275854 A1* | 9/2014 | Venkatraman | A61B 5/721 600/301 |
| 2015/0057511 A1 | 2/2015 | Basu | |

OTHER PUBLICATIONS

"Plethysmograph", Wikipedia, Retrieved on Dec. 5, 2017, Webpage available at : https://en.wikipedia.org/wiki/Plethysmograph.

"Photoplethysmogram (PPG)", Wikipedia, Retrieved on Dec. 5, 2017, Webpage available at : https://en.wiikipedia.org/wiki/Photoplethysmogram.

Extended European Search Report received for corresponding European Patent Application No. 15174687.2, dated Dec. 17, 2015, 8 pages.

International Search Report and Written Opinion received for corresponding Patent Cooperation Treaty Application No. PCT/FI2016/050395, dated Aug. 8, 2016, 12 pages.

Office Action in related Chinese Application No. 201680038992.4, dated Nov. 29, 2019, 14 pages.

Communication Pursuant to Article 94(3) EPC in related European No. 15 174 687.2, dated Apr. 5, 2020, 6 pages.

Second Office Action and Search Report in related Chinese Application No. 201680038992.4, dated Jun. 16, 2020, 13 pages.

Office Action and translation issued in related Chinese Application No. 201680038992.4, dated Nov. 17, 2020, 11 pages.

Substantive Examination Report in related Philippine Invention No. 1/2017/502395, dated Aug. 27, 2020, 5 pages.

* cited by examiner

APPARATUS COMPRISING A LIGHT DETECTOR, A LIGHT SOURCE AND OPTICS

RELATED APPLICATION

This application was originally filed as Patent Cooperation Treaty Application No. PCT/FI2016/050395 filed Jun. 2, 2016 which claims priority benefit to EP Patent Application No. 15174687.2, filed Jun. 30, 2015.

TECHNOLOGICAL FIELD

Embodiments of the present invention relate to an apparatus comprising a light detector, a light source and optics. In particular, they relate to an apparatus that may be used as a photoplethysmography sensor.

BACKGROUND

A photoplethysmogram is an optically obtained plethysmogram as typically used to obtain a volumetric measurement of arterial blood, although other applications are possible. A light source transmits light through the skin of a user into the user's vasculature. The light is reflected by the vasculature and detected by a photo detector. In reflective photoplethysmography the light transmitted from the light source is reflected into the light detector and in transmissive photoplethysmography light transmitted by the light source passes through the target into the light receiver. The light received at the light detector is a function of the components and relevant volumes of those components in the offset region and their optical properties.

One common use of a photoplethysmography sensor is as a pulse reader or as a pulse oximeter.

BRIEF SUMMARY

According to various, but not necessarily all, embodiments of the invention there is provided an apparatus comprising: a light detector; a light source, laterally offset from the light detector by a first lateral offset; optics configured to receive light emitted by the light source and output the received light, wherein a majority of the light output is directed towards an offset region laterally offset from the light detector by at least a second lateral offset different to the first lateral offset.

According to various, but not necessarily all, embodiments of the invention there is provided examples as claimed in the appended claims.

BRIEF DESCRIPTION

For a better understanding of various examples that are useful for understanding the brief description, reference will now be made by way of example only to the accompanying drawings in which.

DETAILED DESCRIPTION

Figure 1:
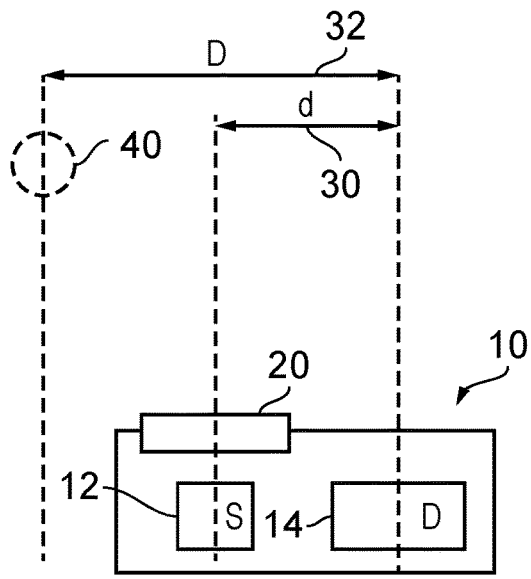
FIG. 1 illustrates an apparatus according to a first embodiment.

In order to make a compact and potentially small scale apparatus 10 it is desirable for a light source 12 at a light detector 14 to be in close proximity. In examples of FIGS. 1 to 3 the light source and the light detector are laterally offset 30 by a distance d. Previously it has been necessary to have this lateral offset distance d greater than 2 mm in certain applications such as reflective photoplethysmography. In this constraint it is necessary to ensure that the optical path length from the light source 12 to the light detector 14 is of sufficient length. The examples described below provide a new type of apparatus 10 comprising a light source 12, a light detector and optics 20. The optics 20 enable the lateral offset between the light source 12 and the light detector 14 to be less than has previously been possible, that is less than 2 mm.

FIG. 1 illustrates an apparatus 10 comprising: a light detector 14; a light source 12, laterally offset 30 from the light detector 14 by a first lateral offset d; optics 20 configured to receive light emitted by the light source 12 and output the received light, wherein a majority of the light output is directed towards an offset region 40 laterally offset 32 from the light detector 14 by at least a second lateral offset D different to the first lateral offset d.

In order to make a compact and potentially small scale apparatus 10 it is desirable for the second lateral offset D to be greater than the first lateral offset d.

Figure 2:
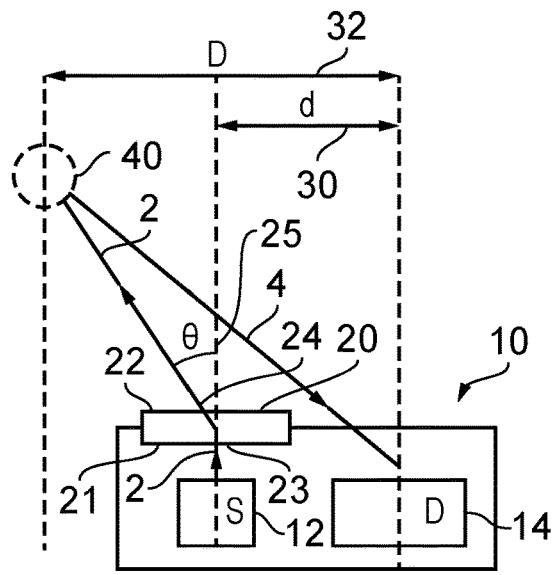
FIG. 2 illustrates an apparatus according to a second embodiment.
Figure 3:
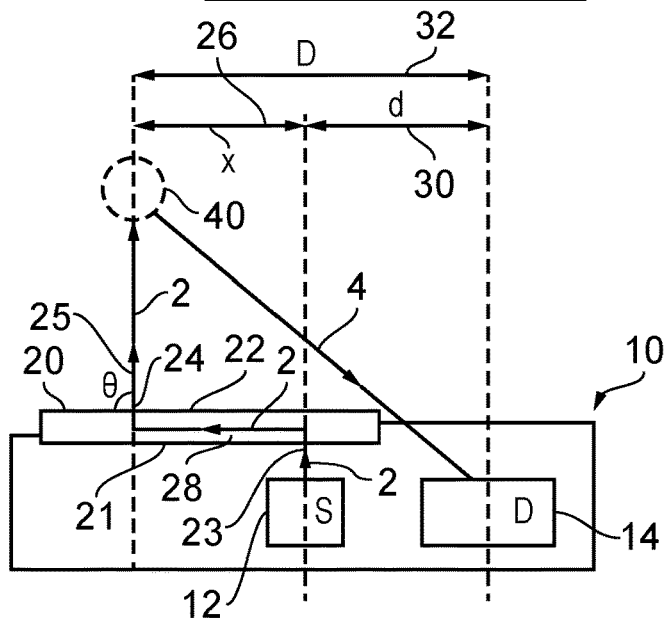
FIG. 3 illustrates an apparatus according to a third embodiment.

FIGS. 2 and 3 illustrate other examples of the apparatus 10 in which different optics 20 are used to redirect a majority of the light 2 received from the light source 12 towards the offset region 40 laterally offset 32 from the light detector 14 by at least a second lateral offset D greater than the first lateral offset d. These figures also illustrate that light reflected from the offset region 40 is detected by the light detector 14.

In some, but not necessarily all embodiments, the first lateral offset is less than 2 mm and the second lateral offset is greater than 2 mm. In some embodiments, the second lateral offset is greater than 5 mm.

In some, but not necessarily all examples, the optics 40 may be configured to defract the received light 2. For example, as illustrated in FIGS. 2 and 3, the optics 20 may have a first side 21 facing towards the light source 12 and a second side 22 facing towards the offset region 40. The first side 21 comprises a light in-coupling region 23 and the second side 22 comprises a light out-coupling region 24. The light in-coupling region is configured to in-couple the light 2 received from the light source 12 at a first angle from a normal to the in-coupling region and the light out-coupling region is configured to out-couple the light 2 at a second angle from a normal 25 to the out-coupling region 24.

In the example illustrated in FIG. 2, the second angle is greater than the first angle and the in-coupling region 23 and the out-coupling region 24 are in close lateral proximity.

In the example illustrated in FIG. 3, the light out-coupling region 24 is laterally offset 26 by a lateral offset X from the light in-coupling region 23. The lateral offset X is the difference between the second lateral offset D and the first lateral offset d in this example. The optics 20 provides a laterally extending light guiding region 28 between the in-coupling region 23 and the out-coupling region 24. This lateral light guiding region 28 is configured to guide the light 2 by total internal reflection between the in-coupling region 23 and the out-coupling region 24. The total internal reflection traps light inside the optics 20 between the in-coupling region 23 and the out-coupling region 24. The optics 20 therefore extends laterally for at least the offset X and in some examples for a distance as large as the second offset D away from the light detector 14. As an example, as illustrated in FIG. 4 the optics 20 may form a window 50 overlying both the light detector 14 and the light source 12.

The in-coupling region 23 may be provided by a diffractive structure or by a refractive element or elements. The out-coupling region 24 may be provided by a diffractive structure pattern or by a refractive element or elements. A diffractive structure may for example be a diffractive optical element, a diffraction grating, a periodic structure or pattern or a series of diffraction lines/slits/grooves.

Figure 4:
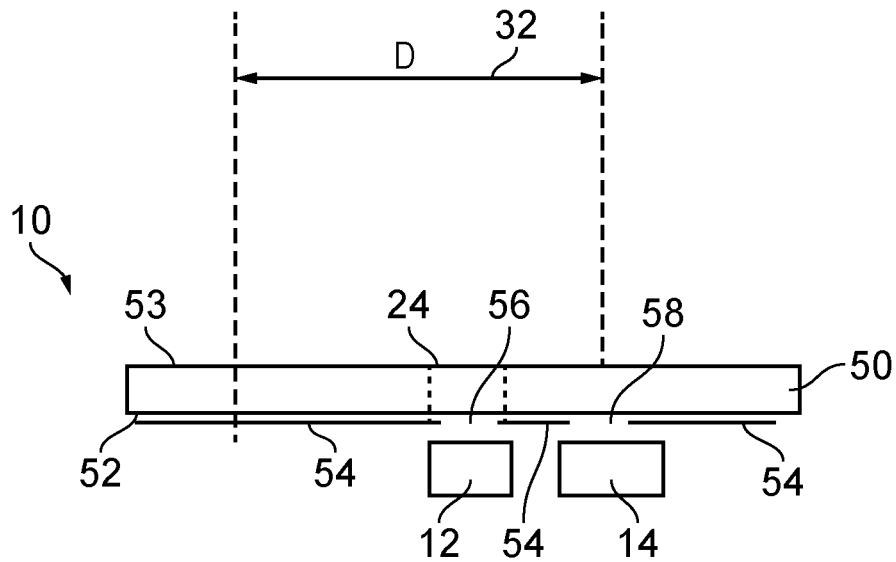
FIG. 4 illustrates another example of optics for an apparatus.

As illustrated in FIG. 4, the window 50 comprises an internal surface 52 (first side 21 of the optics 20) and an external surface 53 (second side 22 of the optics 20). The internal surface 52 is an externally reflective surface 54 such that external light passing through the window 50 to the reflective surface 54 is reflected back through the window 50 externally. The reflective surface 54 may in some examples be a specular reflective surface, for example, a mirrored surface.

The reflective surface 54 comprises an aperture 56 for the light 2 from the light source 12 and an aperture 58 for the light detector 14. The aperture 58 for the light detector 14 is generally aligned with the light detector 14 (no lateral offset). The aperture 56 for the light 2 from the light source 12 is generally aligned with the out-coupling region 24 of the optics 20. In the example of FIG. 2, the aperture 56 would be aligned with the light source 12 and in the example of FIG. 3, the aperture 56 would be aligned with the out-coupling region 24 is laterally offset 26 by a lateral offset X from the light in-coupling region 23.

The reflective surface 54 extends between the out-coupling region 24 and the light detector 14 and increases the amount of light from the light source 12 that ultimately reaches the light detector 14.

The reflective surface 54, in the illustrated example, extends over the internal surface 52 for a distance beyond the second lateral offset D from the light detector 14. The reflective surface is continuous and uninterrupted except for the apertures 56, 58. The reflective surface 54 may extend, in all directions, over the internal surface 52 for a distance beyond the second lateral offset D from the light detector 14 and, in this case, the aperture 56 may have an annular shape and surround the aperture 58.

In the above described examples the light source 12 may be any suitable source of light 2. For example, it may comprise one or more light emitting diodes. The one or more light emitting diodes may transmit light at the same frequency or at different frequencies. The light detector 14 may be any suitable detector of light. For example it may be a photodetector such as a semiconductor photodetector configured, for example, as a photodiode or as a phototransistor.

In the examples of FIGS. 3 and 4, the light output by the light source 12 is directed towards an offset region 40 laterally offset 32 from the light detector 14 by at least a second lateral offset D different to the first lateral offset d. The offset region 40 may for example comprise an annulus of regions that are at the same azimuthal distance from an axis through the light source 12 or light detector 14. The annulus may, for example be symmetric about an axis through the light detector 14 and may have a position displaced along that axis from the light detector 14. The light 2 output by the light source 12 is directed to the whole of the annulus.

Figure 5:
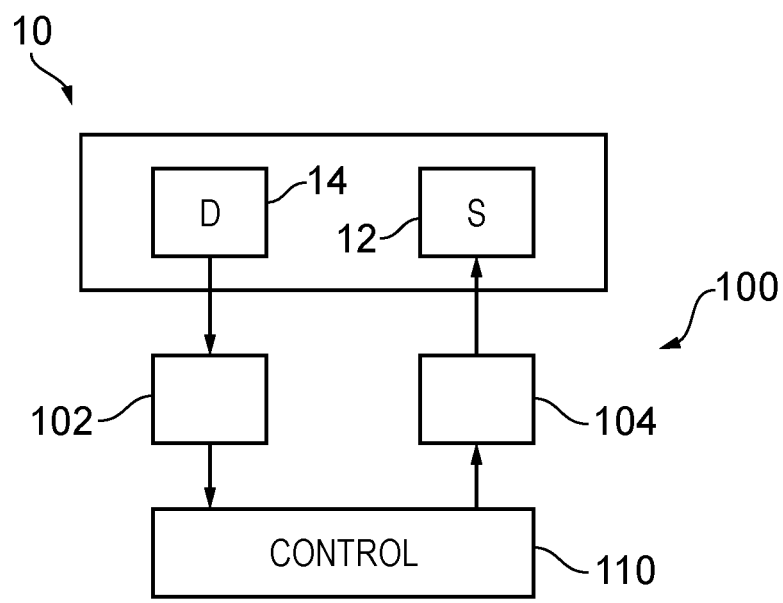
FIG. 5 illustrates a photoplethysmography sensor comprising the apparatus.

FIG. 5 illustrates a photoplethysmography system 100 comprising the apparatus 10. The system 100 comprises driving circuitry 104 for driving the light source 12 of the apparatus 10 and detection circuitry 102 for receiving an output from the light detector 14 of the apparatus 10.

In order to obtain a desired signal from the offset region, it may be desirable to use signal processing to separate the desired signal from undesired signal.

For example, in some but not necessarily all embodiments the offset region 40 may comprise an arterial blood supply that pulsates. The pulsating blood has a time varying absorption which causes the light detector 14 to produce a signal with a relatively small time varying component. Extraction of the time varying component associated with the pulse by detection circuitry 102 provides information specific to the pulsating blood. For example, according to the Beer Lambert law the absorption will depend upon absorptivity of the blood components, concentration of the blood components and a light path length through the arterial blood.

The apparatus 10 may be configured to compare absorption at different frequencies of light for the same offset region 40 at the same time.

The apparatus 10 may be configured to determine the relative concentrations of analytes in the offset region 40 as the light path length through the arterial blood for both light detectors will be the same. This analysis may be performed by the apparatus 10, operating as a pulse oximeter, using red and infrared light, to determine a concentration of oxyhaemoglobin.

In some but not necessarily all examples, control circuitry 110 is connected to both the driving circuitry 104 and the detection circuitry 102. The control circuitry 110 may for example operate the light source 12 and the light detector 14 in a coordinated or synchronized manner to reduce noise. For example, the driving circuitry 104 may modulate, in time, the amplitude and/or frequency of the light source enabling the separation of a detected light 4 arising from the light source 12 from that arising from ambient light.

In some but not necessarily all examples, the control circuitry 110 may for example operate the light source 12 and the light detector 14 in a time division duplex fashion such that they are not simultaneously operational but that they operate successfully with a time period that is dependent upon the distance of the offset region 40 from the light source 12 and the light detector 14. It may for example be desirable for the light detector 14 to be switched off when the light source 12 is switched on and for the light detector 14 to be switched on when the light 2 emitted from the light source 12 has been reflected by the offset region 40 and is at the light detector 14. It will be appreciated that the timing of the detection can control the location of a target region within the offset region 40 from which signals are sampled.

Where a structural feature has been described, it may be replaced by means for performing one or more of the functions of the structural feature whether that function or those functions are explicitly or implicitly described.

The light source performs the function of providing light and may be replaced by any suitable lighting means. The light detector performs the function of detecting light and may be replaced by any suitable light detection means. The optics performs the function of laterally offsetting the light from the light source 12 to the offset region 40 and may be replaced by any suitable light offsetting means.

The term 'comprise' is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term 'example' or 'for example' or 'may' in the text denotes, whether explicitly stated or not, that such features or functions are present in at least the described example, whether described as an example or not, and that they can be, but are not necessarily, present in some of or all other examples. Thus 'example', 'for example' or 'may' refers to a particular instance in a class of examples. A property of the instance can be a property of only that instance or a property of the class or a property of a sub-class of the class that includes some but not all of the instances in the class. It is therefore implicitly disclosed that a features described with reference to one example but not with reference to another example, can where possible be used in that other example but does not necessarily have to be used in that other example.

In the foregoing examples, the second lateral offset is greater than the first lateral offset. In other examples, the second lateral offset may be less than the first lateral offset.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. An apparatus comprising:
a light detector;
a light source, laterally offset from the light detector by a first lateral offset; and
optics configured to receive light emitted by the light source and to output the received light, wherein a majority of the light output is directed towards an offset region laterally offset from the light detector by at least a second lateral offset greater than the first lateral offset, and wherein the optics have a first side towards the light source and a second side towards the offset region, and wherein the first side comprises a light in-coupling region and the second side comprises a light out-coupling region, and wherein the light in-coupling region is configured to in-couple the received light at a first angle from a normal to the in-coupling region and the light out-coupling region is configured to out-couple the light at a second angle from a normal to the out-coupling region, and wherein the second angle is greater than the first angle.

2. The apparatus as claimed in claim 1, wherein the optics are configured to redirect a majority of the light received towards the offset region laterally offset from the light detector by at least the second lateral offset comprising a greater lateral offset than the first lateral offset.

3. The apparatus as claimed in claim 1, wherein the first lateral offset is less than 2 mm and the second lateral offset is greater than 2 mm.

4. The apparatus as claimed in claim 1, wherein the optics are configured to diffract the received light.

5. The apparatus as claimed in claim 1, wherein the in-coupling region comprises a diffractive structure.

6. The apparatus as claimed in claim 5, wherein the diffractive structure comprises at least one of the following; an optical element, a diffraction grating, a periodical structure, a periodical pattern, a series of diffraction lines, a series of slits, a series of grooves.

7. The apparatus as claimed in claim 1, wherein the in-coupling region comprises at least one reflective element.

8. The apparatus as claimed in claim 1, wherein the light out-coupling region is laterally offset from the light in-coupling region and interconnected by a lateral light guiding region.

9. The apparatus as claimed in claim 1, wherein the optics are comprised in a window overlying both the light detector and the light source and extending laterally for at least the second offset away from the light detector.

10. The apparatus as claimed in claim 1, wherein the optics comprise a reflective surface configured to reflect light received from the offset region and comprising an aperture to emit light from the light source and an aperture to provide light to the light detector.

11. The apparatus as claimed in claim 1, wherein the reflective surface is a mirrored surface on an internal side of the optics.

12. The apparatus as claimed in claim 1, configured as a reflective photoplethysmography sensor or a pulse oximeter.

13. The apparatus as claimed in claim 1, configured as a reflective photoplethysmography sensor or a pulse oximeter comprising driving circuitry for the light source and detection circuitry for the light detector and control circuitry for coordinating operation of the light source and light detector.

14. A method comprising:
enabling optics to receive light emitted by a light source, laterally offset from a light detector by a first lateral offset, and to output at least some of the received light, wherein a majority of the light output is directed towards an offset region laterally offset from the light detector by at least a second lateral offset greater than the first lateral offset, and wherein the optics have a first side towards the light source and a second side towards the offset region, and wherein the first side comprises a light in-coupling region and the second side comprises a light out-coupling region, and wherein the light in-coupling region is configured to in-couple the received light at a first angle from a normal to the in-coupling region and the light out-coupling region is configured to out-couple the light at a second angle from a normal to the out-coupling region, and wherein the second angle is greater than the first angle.

* * * * *